United States Patent [19]

Portenhauser et al.

[11] Patent Number: 5,071,767
[45] Date of Patent: Dec. 10, 1991

[54] PROCESS FOR THE DETERMINATION OF FRUCTOSAMINE IN BODY FLUIDS AND CALIBRATION SOLUTION

[75] Inventors: Rudolf Portenhauser; Bernd Vogt, both of Tutzing, Fed. Rep. of Germany

[73] Assignee: Boehringer Mannheim GmbH, Mannheim, Fed. Rep. of Germany

[21] Appl. No.: 375,746

[22] Filed: Jul. 5, 1989

[30] Foreign Application Priority Data

Jul. 5, 1988 [DE] Fed. Rep. of Germany ....... 3822749

[51] Int. Cl.$^5$ ...................... G01N 33/66; G01N 33/68
[52] U.S. Cl. .......................................... 436/15; 436/8; 436/14; 436/87; 436/88; 436/95; 530/322; 530/395
[58] Field of Search ................... 436/8, 14, 15, 67, 87, 436/88, 95, 904, 164; 422/61; 252/408.1; 530/322, 345, 380, 389, 395, 402, 406, 410

[56] References Cited

U.S. PATENT DOCUMENTS

| | | | |
|---|---|---|---|
| 4,274,978 | 6/1981 | Moore | 436/14 |
| 4,629,692 | 12/1986 | Dean | 436/67 X |
| 4,642,259 | 2/1987 | Baker | 436/87 |
| 4,645,742 | 2/1987 | Baker | 436/15 |
| 4,665,192 | 5/1987 | Cerami | 435/7.93 X |

OTHER PUBLICATIONS

Day et al, J. Bio. Chem., vol. 254, No. 3, pp. 595–597, 1979.
Kennedy et al, Diabetes, vol. 29, pp. 413–415, 1980.

*Primary Examiner*—Robert J. Hill, Jr.
*Attorney, Agent, or Firm*—Felfe & Lynch

[57] ABSTRACT

For the determination of fructosamine in body fluids a solution containing fructosamine and albumin is used as the standard solution for calibration which standard solution is essentially free of glucose and which has a pH between 5.0 and 6.0 and contains at least 10 mmol/l buffer.

7 Claims, No Drawings

PROCESS FOR THE DETERMINATION OF FRUCTOSAMINE IN BODY FLUIDS AND CALIBRATION SOLUTION

SUMMARY

The invention concerns a process for the determination of fructosamine in body fluids as well as a suitable standard solution therefor.

Under the metabolic conditions of diabetes proteins are glycosylated by the surplus glucose present in the blood. In this process the carbonyl group of glucose reacts first with free amino groups of proteins to form Schiff bases. Fructosamines, which have a stable ketoamine linkage, are then formed by Amadori rearrangement. Because of the stability of this ketoamine linkage the half-life of fructosamine is practically identical with that of serum proteins. This non-enzymatic glycosylation of proteins seems to be the cause of various functional disorders which are especially prevalent in diabetics. It is therefore important to monitor the formation of glycosylated proteins. Up to now glycosylated haemoglobin, which is referred to as $HbA_1$, has been measured as an indicator. The monitoring of this parameter is suitable for a long-term control of the sugar metabolism. Since glycosylated haemoglobin reveals only long-term changes in metabolism because of its long half-life and since short-term fluctuations in metabolism are not discernible because of the slowness of haemoglobin catabolism, this parameter is not suitable for an intermediate-term control of metabolic regulation. On the other hand the sugar metabolism in diabetics can be monitored by measurement of the blood glucose concentration. Since the blood glucose concentration is subject to great fluctuations it only gives the physician information about the metabolic condition at the time the blood sample was taken. This gap between short-term monitoring of the blood glucose concentration and long-term control by measurement of $HbA_{1c}$ is now filled by the determination of glycosylated proteins called fructosamines. Various studies have shown that the determination of serum fructosamine is a reliable, specific and practicable method for monitoring diabetics.

Known methods for the determination of fructosamines as described for example in Johnson et al., Clin. Chem. Acta (1982) 127, 87–95, are based on the conversion of fructosamine, which is present under aqueous alkaline conditions in the enol form and which can easily be oxidized in this form, by an oxidizing agent, which is coloured in the reduced form, for example a tetrazolium salt. The coloured formazan which thereby forms can then be measured photometrically and is proportional to the amount of fructosamine.

In order to allow an exact determination it is necessary to establish calibration curves with standard solutions, so that the value obtained in a determination of a sample solution may be ascertained by comparison with the calibration curve. Furthermore it is necessary to use standard solutions with known content to check the precision of methods of determination and to calibrate automated analysers. Standard solutions which are used for this purpose must contain the parameter to be measured in known concentrations. The concentration of the parameter must be in the medically relevant measuring range. The standard solutions must be simple to handle and above all they must have as long a stability as possible.

Standard solutions for the determination of fructosamine known up to now do not fulfill some or all of these requirements. On the one hand control sera or calibration sera are used which simulate the serum fructosamine concentration in the form of model substances. Usually 1-deoxy-1-morpholino-fructose (DMF) is used for this. The disadvantage of this known standard solution is that the model substance DMF behaves completely differently to serum fructosamines, so that a comparison of the measured values with a calibration curve which has been established using DMF cannot yield exact concentrations. Therefore the values obtained in this way are referred to as DMF-units.

Other known standard solutions containing serum fructosamine show a considerable instability of the serum fructosamine concentration after storage for several days at 35° C. An increase of 200% and more was observed which can be accounted for by a continuing non-enzymatic protein glycosylation.

The object of the present invention was therefore to provide a standard solution for the determination of serum fructosamine which is easy to handle, whose concentration is easily adjustable and which can be stored for long periods without losing its stability.

This object was achieved by a process for the determination of fructosamine in body fluids, wherein a solution containing fructosamine and albumin is used as the standard solution for calibration, which is essentially free of glucose and which has a pH between 5.0 and 6.0 and contains at least 10 mmol/l buffer.

In accordance with the present invention a standard solution is provided which contains the parameter serum fructosamine in a form which is similar to or even identical with glycosylated serum protein. This solution is surprisingly stable during storage for longer periods and is therefore suitable for long-term storage.

In the process according to the present invention a solution containing albumin is used as standard solution. This solution containing albumin serves as the protein matrix. Suitable for this are for example aqueous solutions of human serum albumin or bovine serum albumin. Especially preferred as the solution containing albumin is human serum.

It is important that the solution containing albumin is essentially free of glucose so as to ensure a long storage stability. In order to use human serum it must therefore be freed of glucose. This can be achieved for example by dialyzing human serum against a buffer containing all naturally occurring serum components except glucose. Especially preferred is dialysis against a medium containing 150 mmol/l NaCl, 10 mmol/l sodium phosphate and which has been adjusted with NaOH to a pH of from 6.0 to 8.0.

The solution containing albumin has to contain in addition serum fructosamine in a known amount. When using human serum, endogenous fructosamine is already present. To solutions of albumin, fructosamine has to be added. Both types of solution can be supplemented with additional fructosamine in order to obtain a desired fructosamine content.

For this purpose it is preferable to add artificially glycosylated serum albumins to the solution containing albumin and to adjust the concentration of serum fructosamine as required. Normal and pathological serum fructosamine concentrations can be obtained by varying the amounts added. The preparation of serum fructosamine can be carried out for example analogous to the procedure described by J. F. Day et al., in J. Biol. Chem. 254 No. 3 (1979) 595-597. An aqueous serum albumin solution is incubated with glucose for 8 days at 25° C. and subsequently dialyzed to remove free glucose.

The standard solution is adjusted to a pH in the range of between 5.0 and 6.0 by addition of a buffer system. Since the isoelectric point for serum albumin is at a pH of 4.9, a pH lower than 5.0 leads to a slight turbidity due to protein precipitation. At a pH above 6.0 a satisfactory storage stability could not be achieved. Especially preferred for the standard solution is a pH in the range of 5.4 to 5.9.

The pH is adjusted by addition of a buffer solution. The concentration of this buffer is higher than 10 mmol/l. Preferably the buffer is added in a concentration of 10 to 70 mmol/l. Buffer systems with a pH in the preferred range are suitable for the buffer. Especially preferred is phosphate buffer.

In addition, the standard solution can contain substances which are usually present in calibration sera. Clarifying agents, stabilizing agents, detergents and preserving agents can for example be added. Pentaerythritol can for example be used as the clarifying agent. Zinc and EDTA are especially suitable as stabilizing agents. Phenols or antibiotics can for example be used a preserving agents. Other auxiliary agents known to the expert can also be used.

The preparation of the standard solution according to the present invention is carried out by mixing the individual components and adjustment of the pH by addition of the buffer system.

Usually the standard solution is sterilized afterwards by filtration and lyophilized for longer storage.

A further embodiment of the present invention is a standard solution for the determination of fructosamine in body fluids, wherein a solution containing fructosamine and albumin, which is essentially free of glucose, contains a buffer at a concentration of more than 10 mmol/l and has a pH in the range of 5.0 to 6.0.

The standard solution used in accordance with the present invention is remarkably stable. It yields steep calibration curves, which allow the accurate and sensitive determination of fructosamine.

The following examples elucidate the present invention.

Example 1

300 ml human serum with a protein content of 60 g/l which had been deep-frozen within a few hours after isolation was thawed and dialyzed. Dialysis was carried out twice for six hours against an approximately fortyfold volume of a buffer with a pH of 6.5 and which contained 150 mmol/l NaCl and 10 mmol/l $NaH_2PO_4$. After dialysis the serum, which no longer contained any detectable glucose was filtered (EKS I-filter, Schleicher & Schüll Company) in order to remove microorganisms and after addition of $ZnCl_2$ (0.1 mmol/l) and Titriplex III (1.0 mmol/l) the pH of the serum was adjusted to 5.9±0.1.

Afterwards the endogenous serum fructosamine concentration was determined.

In addition glycosylated human serum albumin was prepared as follows:

254 g glucose (anhydrous) was added to 280 ml sterile physiological saline. 2 g (=29.4 mmol) human serum albumin was added to the solution and gently stirred in the dark for 8 days at 25° C. Afterwards the solution was dialyzed against distilled water until free of glucose and subsequently concentrated (exclusion limit 10 000) and lyophilized.

The fructosamine content thus obtained was about 3 to 8 times higher than that of the endogenous serum fructosamine in the original material. Measurement was carried out with the colorimetric test described in the introduction.

The preparation was carried out according to the method described by J. F. Day et al., J. Biol. Chem. 254 No. 3 (1979) 595-597.

Standard solutions were prepared by adding glycosylated human serum albumin, in an amount calculated to achieve the required fructosamine concentration, to the dialyzed human serum, obtained as described above, and dissolving it by stirring.

The solution thus obtained was filtered through a membrane filter with a mesh size of $\leq 2$ µm to remove microorganisms; 1 ml aliquots were then dispensed into bottles and lyophilized. The lyophilisate prepared in this way contained a serum fructosamine concentration of 0.27 mmol/l on reconstitution with 1.0 ml re-distilled water.

Example 2

600 ml of fresh human plasma with a protein content of 50 g/l was converted to human serum by recalcification and removal of the clot. The serum was evaporated to about ⅔ of its original volume i.e. about 400 ml, whereby the protein concentration was changed to 63 g/l. Dialysis addition of $ZnCl_2$ and Titriplex III, pH adjustment and measurement of the endogenous fructosamine concentration was carried out as described in Example 1.

The calculated amount of glycosylated human serum albumin, needed to obtain the required concentration of fructosamine for the calibration serum, was dissolved in human serum as described in Example 1. After filtration and dispensing in 1 ml aliquots, lyophilization was carried out. The lyophilisate thus obtained contained a serum fructosamine concentration of 0.38 mmol/l after reconstitution with 1.0 ml re-distilled water.

Example 3

A standard solution with a fructosamine content in the pathological range was prepared.

For this purpose 300 ml of an aqueous solution of bovine serum albumin (6% by weight), which was depleted of glucose by dialysis, was treated as described in Example 1. The calculated amount of glycosylated bovine serum albumin needed to obtain the required concentration of fructosamine was dissolved in the bovine serum albumin solution by stirring as described in Example 1. The bovine serum albumin solution was then filtered through a membrane filter with a mesh size of $\leq 2$ µm to remove microorganisms, 1 ml aliquots were dispensed into bottles and lyophilized.

The lyophilisate, prepared in this way, had a serum fructosamine concentration of 0.49 mmol/l after reconstitution with 1. ml re-distilled water.

We claim:

1. A process for the determination of fructosamine in body fluid comprising
   measuring a characteristic of the body fluid that is related to the amount of fructosamine in the body fluid, and comparing the measured characteristic with one obtained with a standard solution containing a known amount of fructosamine and albumin and wherein said standard solution is essentially free of glucose, has a pH of 5.0–6.0 and contains at least 10 mmol/l buffer.

2. The process of claim 1 wherein the albumin is human serum albumin or bovine serum albumin.

3. The process of claim 1 or 2 wherein the standard solution containing albumin is dialyzed, buffered human serum at pH 5.0–6.0.

4. The process of claim 1 or 2 wherein the standard solution has a pH between 5.4 and 5.9.

5. The process of claim 1 or 2 wherein the standard solution has 10 to 70 mmol/l buffer.

6. The process of claim 1 or 2 wherein the buffer is a phosphate buffer.

7. A standard solution for the determination of fructosamine comprising fructosamine, albumin and at least 10 mmol/l buffer, wherein the standard solution has a pH in the range of 5.0 to 6.0 and is essentially free of glucose.

* * * * *